United States Patent [19]

Heywang et al.

[11] 4,357,329
[45] Nov. 2, 1982

[54] COMBATING PESTS WITH N-PHOSPHONYLCARBONYL-CARBAMATES

[75] Inventors: Gerhard Heywang; Engelbert Kühle, both of Bergisch-Gladbach; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 276,406

[22] Filed: Jun. 22, 1981

[30] Foreign Application Priority Data

Jul. 11, 1980 [DE] Fed. Rep. of Germany ....... 3026326

[51] Int. Cl.³ .................... A01N 57/24; A01N 57/22; C07F 9/40
[52] U.S. Cl. .................... 424/212; 424/202; 424/203; 424/204; 424/209; 548/262; 549/14; 549/21; 549/30; 549/38; 260/453.3; 260/453.8; 260/931; 260/938; 549/220
[58] Field of Search ........... 260/346.73, 938, 340.5 R, 260/340.7, 340.9, 453.3, 453.8, 931; 548/262; 549/14, 21, 30, 38; 424/202, 203, 204, 209, 212

[56] References Cited

U.S. PATENT DOCUMENTS 4,043,794  8/1977  Sauers ..................................... 71/86

FOREIGN PATENT DOCUMENTS 2142496  8/1971  Fed. Rep. of Germany .
2132936  1/1973  Fed. Rep. of Germany .
2804664  8/1978  Fed. Rep. of Germany .

OTHER PUBLICATIONS

J. Agr. Food Chem., vol. 18, No. 5, 1970, pp. 793-796.

Primary Examiner—John M. Ford
Assistant Examiner—Bernard Dentz
Attorney, Agent, or Firm—Sprung, Horn, Kramer & Woods

[57] ABSTRACT

N-Phosphonylcarbonyl-N-methylcarbamic acid esters of the formula

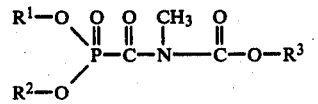

in which
$R^1$ and $R^2$ can be identical or different and each represents alkyl, alkenyl or alkynyl, it being possible for any of these radicals to be substituted by halogen, and
$R^3$ represents alkyl, phenyl, naphthyl, benzodioxolanyl, dihydrobenzofuranyl or indanyl, it being possible for any of these radicals to carry one or more substituents selected from alkyl, alkenyl, alkynyl, alkoxy, alkenoxy, alkynoxy, alkylthio, alkenylthio, alkynylthio, dialkylamino, halogenoalkyl, halogen, nitro, cyano, cycloalkyl, formamidino, dioxanyl and dioxolanyl, or
$R^3$ represents a radical of the formula

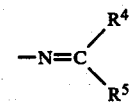

in which
$R^4$ and $R^5$ can be identical or different and each represents alkyl, alkoxy, alkylthio, alkylthioalkyk, cyano, alkoxycarbonyl, dialkylcarbamoyl, dialkoxyphosphoryl or triazolyl, or
$R^4$ and $R^5$, together with the C atom to which they are bonded, form a dithiolane, dithiane, oxythiolane or oxathiane ring which is optionally substituted by methyl or phenyl,
which are pesticidally active.

10 Claims, No Drawings

COMBATING PESTS WITH N-PHOSPHONYLCARBONYL-CARBAMATES

The present invention relates to certain new N-phosphonylcarbonylcarbamates, to a process for their preparation and to their use for combating pests.

It has already been disclosed that N-carbonylated carbamates, such as N-carboxylated N-methylcarbamic acid aryl esters (see U.S. Pat. No. 4,014,923, filed Mar. 29, 1977, and N-chloro-carbonyl-N-methylcarbamic acid aryl esters (see DE-OS (German Published Specification) No. 2,142,496) have insecticidal properties. However, their action is not always completely satisfactory, especially when small amounts are applied.

The present invention now provides, as new compounds, the N-phosphonylcarbonyl-N-methylcarbamic acid esters of the general formula $$\begin{array}{c} R^1-O \quad O \quad O \quad CH_3 \quad O \\ \phantom{R^1-O}\diagdown \| \quad \| \quad | \quad \| \\ \phantom{R^1-O\diagdown}P-C-N\!\!-\!\!-\!\!C-O-R^3 \\ \phantom{R^1-O\diagdown}\diagup \\ R^2-O \end{array} \qquad (I)$$

in which
$R^1$ and $R^2$ can be identical or different and each represents alkyl, alkenyl or alkynyl, it being possible for any of these radicals to be substituted by halogen, and
$R^3$ represents alkyl, phenyl, naphthyl, benzodioxolanyl, dihydrobenzofuranyl or indanyl, it being possible for any of these radicals to carry one or more substituents selected from alkyl, alkenyl, alkynyl, alkoxy, alkenoxy, alkynoxy, alkylthio, alkenylthio, alkynylthio, dialkylamino, halogenoalkyl, halogen, nitro, cyano, cycloalkyl, formamidino, dioxanyl and dioxolanyl, or
$R^3$ represents a radical of the general formula $$-N=C\diagup^{R^4}_{\diagdown R^5} \qquad (Ia)$$

in which
$R^4$ and $R^5$ can be identical or different and each represents alkyl, alkoxy, alkylthio, alkylthioalkyl, cyano, alkoxycarbonyl, dialkylcarbamoyl, dialkoxyphosphonyl or triazolyl, or
$R^4$ and $R^5$, together with the C atom to which they are bonded, form a dithiolane, dithiane, oxythiolane or oxathiane ring which is optionally substituted by methyl or phenyl.

It has been found that the compounds of the formula (I) can be used for combating pests, above all arthropods, preferably insects and arachnids, especially insects.

It is decidedly surprising that the compounds of the formula (I) according to the invention have more advantageous properties than the N-carbonylated carbamates known from the state of the art. In substances according to the invention thus represent an enrichment of the art.

The invention also provides a process for the preparation of an N-phosphonylcarbonylcarbamate of the formula (I), in which (a) an N-chlorocarbonyl-N-methylcarbamic acid ester of the general formula $$\begin{array}{c} CH_3 \\ | \\ R^3-O-CO-N-CO-Cl, \end{array} \qquad (II)$$

in which
$R^3$ has the abovementioned meaning, is reacted with a phosphite of the general formula $$\begin{array}{c} R^1-O \\ \phantom{R^1-O}\diagdown \\ \phantom{R^1-O\diagdown}P-O-R^6, \\ \phantom{R^1-O\diagdown}\diagup \\ R^2-O \end{array} \qquad (III)$$

in which
$R^1$ and $R^2$ have the abovementioned meanings and $R^6$ represents alkyl, alkenyl or alkynyl, it being possible for any of these groups to be substituted by halogen, and wherein
$R^1$, $R^2$ and $R^6$ can be identical or different, if appropriate in the presence of a diluent, or (b) a phosphite of the formula (III) is reacted with bischloro-carbonyl-N-methylamine of the formula $$\begin{array}{c} CH_3 \\ | \\ Cl-CO-N-CO-Cl, \end{array} \qquad (IV)$$

and a hydroxy compound of the general formula $$R^3-OH \qquad (V),$$

in which
$R^3$ has the abovementioned meaning, if appropriate in the presence of an acid-binding agent and/or of a diluent.

If, for example, 2,3-dihydro-2,2-dimethyl-7-benzofuranyl N-chlorocarbonyl-N-methyl-carbamate (formula IV) and triethyl phosphite (formula VII) are used as starting substances, the course of the reaction in process variant (a) can be represented by the following equation:

Equation 1

If, for example, 1-methylthio-acetaloxime (formula VIII), bischlorocarbonyl-N-methylamine (formula IV) and trimethyl phosphite (formula IX) are used as starting substances, the course of the reaction in process variant (b) can be represented, for example, by the following equation:

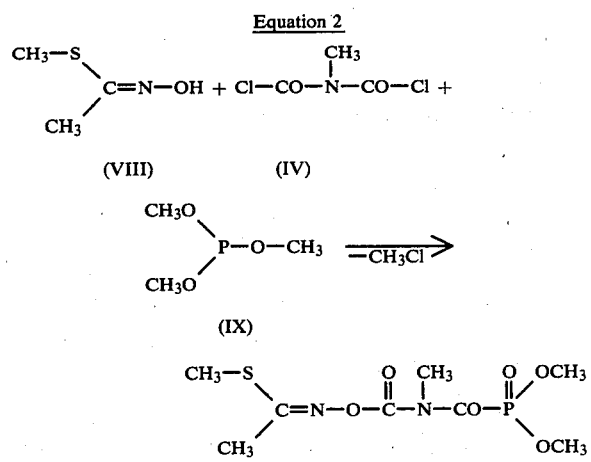

The phosphites, N-chlorocarbonyl-N-methylcarbamic acid esters, phenols, oximes and bischlorocarbonylmethylamine used as starting substances are known.

Phosphites of the formula (III) in which $R^1$, $R^2$ and $R^6$ are identical and represent methyl, ethyl, 2-chloroethyl, octyl, allyl or propargyl, are preferably used.

If N-chlorocarbonyl-N-methylcarbamic acid esters are used as the starting compounds of the formula (II), $R^3$ preferably represents a phenyl, 2-isopropylphenyl, 3-isopropylphenyl, 2-isopropoxypheny, 3,5-dimethyl-4-methylmercaptophenyl, 3-methyl-4-dimethylaminophenyl, 4-nitrophenyl, 2-allyloxyphenyl, 3-sec.-butyl-4-methylphenyl, 4-methyl-3-isopropylphenyl, 2-dimethylaminophenyl, 2-(1',3'-dioxolan-2'-yl)-phenyl, 2-(4',5'-dimethyl-1',3'-dioxolan-2'-yl)-phenyl, 1-naphthyl, 4-(1,1-dimethylindanyl), 2,2-dimethylbenzodioxolanyl or 2,2-dimethyl-2, 3-dihydrobenzofuran-7-yl-or a methyl radical.

If phenols are used as starting compounds of the formula (V), $R^3$ preferably represents a phenyl, 2-isopropylphenyl, 3-isopropylphenyl, 2-isopropoxyphenyl, 3,5-dimethyl-4-methylmercaptophenyl, 3-methyl-4-dimethylaminophenyl, 4-nitrophenyl, 2-allyloxyphenyl, 3-sec.-butyl-4-methylphenyl, 4-methyl-3-isopropylphenyl, 2-dimethylaminophenyl, 2-(1',3'-dioxolan-2'-yl)-phenyl, 2-(4',5'-dimethyl-1',3'-dioxolan-2'-yl)-phenyl, 1-naphthyl, 4-(1,1-dimethylindanyl), 2,2-dimethylbenzodioxolanyl or 2,2-dimethyl-2,3-dihydrobenzofuran-7-yl radical.

If oximes are used as starting compounds of the formula (V), oximino-malonic acid diethyl ester, 2-oximino-1,3-dithiolane, 4-methyl-2-oximino-1,3-dithiolane, 4,4-dimethyl-2-oximino-1,3-dithiolane, 4-phenyl-2-oximino-1,3-dithiolane, 2-oximino-1,3-oxathiolane, 2-oximino-1,3-dithiane, 2-oximino-1,3-oxathiane, hydroxamothioacetic acid S-methyl ester, α-methylmercapto-α-oximino-acetic acid ethyl ester, α-methylmercapto-α-oximino-N,N-dimethylacetamide, β,β-dimethyl-α-oximino-butyronitrile or 2,2-dimethyl-1-oximino-1-triazolylpropane can preferably be used.

The radicals in the formulae preferably have the following meanings:

Alkyl $R^1$, $R^2$, $R^3$, $R^4$, $R^5$ and $R^6$ and the alkyl substituents and halogenoalkyl substituents possible in $R^3$ are straight-chain or branched and preferably contain 1 to 8, especially 1 to 4, carbon atoms, examples which may be mentioned being methyl, ethyl, n- and i-propyl and n-, i-, s- and t-butyl. Halogenomethyl, preferably trichloromethyl and trifluoromethyl, may be mentioned as examples of the halogenoalkyl substituent in $R^3$.

Alkenyl and alkynyl $R^1$, $R^2$ and $R^6$ and the alkenyl and alkynyl substituents possible in $R^3$ are straight-chain or branched and preferably contain 2 to 6, especially 3 or 4, carbon atoms, allyl and propargyl being mentioned as examples.

Alkoxy and alkylthio $R^4$ and $R^5$ and as possible substituents in $R^3$ are straight-chain or branched and preferably contain 1 to 6, especially 1 to 4, carbon atoms, examples which may be mentioned being methoxy, methylthio, ethoxy, ethylthio, n-, i- and t-butoxy and n-, i- and t-butyl.

Alkenoxy, alkynoxy, alkenylthio and alkynylthio as possible substituents in $R^3$ are straight-chain or branched and preferably contain 2 to 6, especially 2 to 4, carbon atoms.

Dialkylamino as a possible substituent in $R^3$ and dialkoxyphosphonyl and dialkylcarbamoyl $R^4$ and $R^5$ preferably contain 1 to 4, especially 1 or 2, carbon atoms in each straight-chain or branched alkyl group.

Alkoxycarbonyl $R^4$ and $R^5$ preferably contain 2 to 6, especially 2 to 4, carbon atoms.

Alkylthioalkyl $R^4$ and $R^5$ are straight-chain or branched and preferably contain 2 to 6, especially 2 to 4, carbon atoms, methylthiomethyl and ethylthiomethyl being mentioned as examples.

Cycloalkyl as a possible substituent in $R^3$ contains 3 to 7, preferably 5 or 6, ring carbon atoms.

Halogen in each case denotes fluorine, chlorine, bromine or iodine, preferably fluorine, chlorine or bromine and especially chlorine or fluorine.

Substituted radicals are monosubstituted or polysubstituted by identical or different substituents. They preferably carry 1 to 5, especially 1 to 3, substituents.

Preferred compounds of the formula (I) are those in which $R^1$ and $R^2$ can be identical or different and each represents straight-chain or branched alkyl with 1–8 C atoms, alkenyl with 3 to 6 C atoms or alkynyl with 3–6 C atoms, it being possible for $R^1$ and $R^2$ optionally to be substituted by 1–3 halogen atoms, and $R^3$ represents phenyl, naphthyl, benzodioxolanyl, dihydrobenzofuranyl or indanyl, it being possible for any of these radicals to carry one or more substituents selected from alkyl, alkenyl, alkynyl, alkoxy, alkenoxy, alkynoxy, alkylmercapto, alkenylmercapto, alkynylmercapto and dialkylamino with in each case up to 4 C atoms, and trihalogenomethyl, halogen, nitro, cyano, cycloalkyl, formamidino, dioxanyl and dioxolanyl, or $R^3$ represents the radical of the general formula

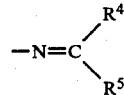

in which $R^4$ and $R^5$ can be identical or different and each represents alkyl, alkoxy or alkylthio, with in each case 1 to 4 carbon atoms, cyano, alkoxycarbonyl or alkylthioalkyl with 2 to 4 carbon atoms, dialkylcarbamoyl or dialkoxyphosphoryl with 1 to 4 carbon atoms per alkyl group, or triazolyl, or R⁴ and R⁵, together with the C atom to which they are bonded, form a dithiolane, dithiane, oxythiolane or oxathiane ring with is optionally substituted by methyl or phenyl.

Particularly preferred N-phosphonylcarbonyl-N-carbamates of the general formula (I) are those in which R¹ and R² represent methyl, ethyl, 2-chloroethyl, octyl, allyl or propargyl and R³ represents methyl, or represents phenyl which optionally carries one or more substituents selected from alkyl with 1 to 3 C atoms, alkoxy with 1 to 3 C atoms, methylthio, dioxolanyl and methyl-substituted dioxolanyl, or represents benzodioxolanyl or dihydrobenzofuranyl, it being possible for either of these radicals optionally to be substituted by methyl, or R³ represents naphthyl or the imino radical of the general formula

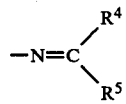

wherein

R⁴ and R⁵ represents alkyl with 1 to 4 C atoms, alkylthioalkyl with 2 to 4 carbon atoms, methylthio, cyano, dimethylaminocarbonyl or ethoxycarbonyl, or R⁴ and R⁵, together with the adjacent C atom to which they are bonded, form a dithiolane ring.

Suitable diluents in the process according to the invention (variants (a) and (b)) are virtually any of the inert organic solvents. These include ethers, such as diethyl ether, dioxane or tetrahydrofuran; hydrocarbons, such as benzene or toluene; halogenated benzenes, such as chlorobenzene and dichlorobenzene; nitriles, ketones and esters; and mixtures of any of these solvents.

If the synthesis of the N-phosphonylcarbonyl-N-methylcarbamates is carried out according to variant (b), a suitable base customary for such reactions is added to the reaction mixture as an acid-binding agent in order to bond the hydrogen chloride formed, a tertiary organic base, for example triethylamine or dimethylbenzylamine, preferably being employed.

The reaction temperatures in process variants (a) and (b) can be varied within a substantial range. In general, the reaction is carried out at between 0° and 100° C., preferably at 20° to 60° C.

The reactants are usually employed in equimolar proportions; it is certainly also possible to use one component in excess, but this provides no substantial advantages.

The active compounds are well tolerated by plants, have a favorable level of toxicity to warm-blooded animals, and are suitable for combating arthropod pests, especially insects and arachnids, and nematode pests, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.;

from the order of the Anoplura, for example *Phylloxera vastatrix, Pemphigus* spp., *Pediculus humanus corporis, Haematopinus* spp. and *Linognathus* spp.;

from the order of the Mallophaga, for example *Trichodectes spp.* and *Damalinea spp.;* from the order of the Thysanoptera, for example *Hercinothrips femoralis* and *Thrips tabaci;* from the order of the Heteroptera, for example *Eurygaster* spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Irialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp.;* from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hyper postica, Dermestes spp., Irogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica;* from the order of the Hymenoptera, for example *Diprion spp., Hoplocampa spp., Lasius spp., Monomorium pharaonis* and *Vespa spp.*;

from the order of the Diptera, for example *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa*;

from the order of the Siphonaptera, for example *Xenopsylla cheopis* and *Ceratophyllus spp.*

The active compounds can be converted into the customary formulations, such as solutions, emulsions, suspensions, powders, dusting agents, foams, pastes, soluble powders, granules, aerosols, suspension-emulsion concentrates, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesive such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their formulations in any of the types that are commercially available and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by micro-organisms and the like.

The active compounds according to the invention can furthermore be present in their formulations in any of the types that are commercially available and in the use forms, prepared from these formulations, as a mixture with synergistic agents. Synergistic agents are compounds which increase the action of the active compounds, without it being necessary for the synergistic agent added to be active itself.

The active compound content of the use forms prepared from the formulations of the types that are commercially available can vary within wide limits. The active compound concentration of the use forms can be from 0.0000001 to 100% by weight of active compound, preferably between 0.0001 to 1% by weight.

The compounds may be employed in a customary manner appropriate for the use forms.

When used against pests harmful to health and pests of stored products, the active compounds are distinguished by an excellent residual action on wood and clay as well as a good stability to alkali on limed substrates.

The active compounds according to the invention are also suitable for combating ectoparasites, the active compounds according to the invention being applied in a known manner.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular arthropods, especially insects) which comprises applying to the pests, or to a habitat thereof, a compound of the present invention alone or in the form of a composition containing as active ingredient a compound of the present invention in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The process according to the invention may be illustrated by the following preparative examples.

I. Method according to variant (a)

EXAMPLE 1

2,3-Dihydro-2,2-dimethyl-7-benzofuranyl N-dimethoxyphosphonylcarbonyl-N-methyl-carbamate

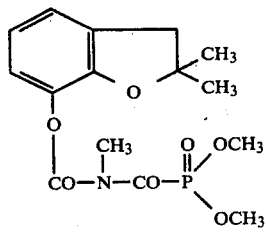
(I)

6 ml of trimethyl phosphite were slowly added dropwise to 14.1 g of 2,3-dihydro-2,2-dimethyl-7-benzofuranyl N-chlorocarbonylcarbamate, while stirring. The exothermic reaction was maintained at 20°–30° C. by external cooling with ice. When the evolution of gas had ended, the volatile constituents were removed under a waterpump vacuum, at a final temperature of 80° C. A viscous oil remained as the residue.

1H-NMR in DCCl$_3$: $\delta$=1.48 ppm (6 H, s, 2 CH$_3$), $\delta$=3.02 ppm (2 H, s, —CH$_2$), $\delta$=3.32 ppm (3 H, s, N—CH$_3$), $\delta$=3.86 ppm (6 H, d, J=11.5 Hz, P(O—CH$_3$)$_2$) and $\delta$=6.95 ppm (3 H, m, aromatic protons).

Yield: 17.4 g (98%).

Further phosphonylcarbonylcarbamates which could be synthesized by this method are summarized in the following table.

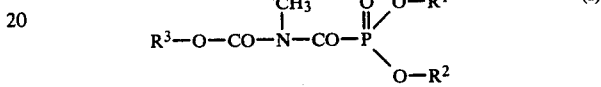
(I)

| Compound No. | R³ | R¹ | R² | Yield (% of theory) | |
|---|---|---|---|---|---|
| 2 | benzofuranyl (CH₃, CH₃) | —C₂H₅ | —C₂H₅ | 100% | $n_D^{20}$ 1.5101 |
| 3 | benzofuranyl (CH₃, CH₃) | —CH₂—CH₂Cl | —CH₂—CH₂Cl | 77% | melting point: 114° C. |
| 4 | CH₃-S-phenyl(CH₃)₂ | CH₃ | —CH₃ | 87% | melting point: 88–89° C. |
| 5 | CH₃-S-phenyl(CH₃)₂ | —C₂H₅ | —C₂H₅ | 91% | melting point: 48–50° C. |
| 6 | CH₃-S-phenyl(CH₃)₂ | —CH₂—CH₂Cl | —CH₂—CH₂Cl | 82% | $n_D^{20}$ = 1.4590 |
| 7 | naphthyl | —CH₃ | CH₃ | 77% | solidified oil |
| 8 | naphthyl | —CH₂—CH₃ | —CH₂—CH₃ | 73% | melting point: 39–41° C. |
| 9 | naphthyl | —CH₂—CH₂—Cl | —CH₂—CH₂—Cl | 77% | $n_D^{20}$ = 1.5748 |

| Compound No. | R³ | R¹ | R² | Yield (% of theory) | |
|---|---|---|---|---|---|
| 10 | 2-(isopropoxy)phenyl | CH₃ | CH₃ | 98% | $n_D^{20} = 1.5068$ |
| 11 | 2-(isopropoxy)phenyl | C₂H₅ | C₂H₅ | 98% | $n_D^{20} = 1.4978$ |
| 12 | 2-(isopropoxy)phenyl | —CH₂—CH₂—Cl | —CH₂—CH₂—Cl | 93% | $n_D^{20} = 1.5170$ |
| 13 | phenyl | CH₃ | CH₃ | 96% | $n_D^{20} = 1.5176$ |
| 14 | CH₃ | CH₃ | CH₃ | 66% | Boiling point 118° C./0.08mbar |

II. Method according to variant (b)

EXAMPLE 2

O-(N-Dimethoxyphosphonylcarbonyl-N-methyl-carbamyl)-hydroxamo-thioacetic acid S-methyl ester

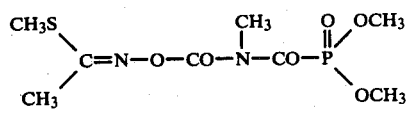 (15)

10.5 ml of bischorocarbonylmethylamine were initially introduced into 50 ml of absolute ether or toluene, and 11.75 ml of trimethyl phosphite were added dropwise at a temperature of 10° C. When the addition had ended, the mixture was subsequently stirred for 10 minutes, 10.5 g of hydroxamothioacetic acid S-methyl ester were then introduced in portions and 14 ml of triethylamine were added dropwise in a manner such that the reaction temperature always remained below 10° C. After stirring the reaction mixture for 2 hours, 100 ml of water were added at 5° C. and the mixture was extracted several times with the solvent employed. After drying the product phase over sodium sulphate, the solvent was removed in vacuo and the residue was triturated with diisopropyl ether. 4 g (13.5%) of a product with a melting point of 88° C. were thus obtained.

calculated: C:32.2; H:5.0; N:9.3; O:32.2; found: C:32.4; H:5.2; N:9.2; O:31.6.

Further phosphonylcarbonylcarbamates obtained by this method are summarized in the following table:

| Compound No. | R³ | R¹ | R² | Yield (% of theory) | |
|---|---|---|---|---|---|
| 16 | (CH₃)₃C—C(=N—)—CH₂—S—CH₃ | CH₃ | CH₃ | 62% | melting point: 90° C. |
| 17 | (CH₃)₃C—C(=N—)—N(pyrazolyl) | CH₃ | CH₃ | 18% | melting point: 102° C. |
| 18 | (CH₃)₃C—C(=N—)—CN | CH₃ | CH₃ | 58% | melting point: 117° C. |
| 19 | 2,2-dimethyl-7-methyl-benzofuran-type | —CH₂—CH₂—Cl | CH₂—CH₂—Cl | 60% | melting point: 112–113° C. |

| Compound No. | R³ | R¹ | R² | Yield (% of theory) |
|---|---|---|---|---|
| (Identical to compound 3 from Example 1). | | | | |

The pesticidal activity of the compounds of this invention is illustrated by the following examples wherein the compounds according to the present invention are each identified by the number (given in brackets) from preparative Examples 1 and 2:

EXAMPLE 3

Myzus test
Solvent: 3 parts by weight of acetone
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (*Brassica oleracea*) which had been heavily infested with peach aphids (*Myzus persicae*) were treated by being dipped into the preparation of active compound of the desired concentration.

After the desired periods of time, the destruction in % was determined. 100% meant that all the aphids had been killed; 0% meant that none of the aphids had been killed.

In this test, for example, the compounds (1) to (6), (10), (11), (15) and (16) exhibited a degree of destruction of between 70 and 100% in experiments using a concentration of 0.01%.

EXAMPLES 4 AND 5

Critical concentration test/soil insects
(4) Test insect: *Phorbia antiqua* maggots in the soil
(5) Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l), being decisive. The soil was filled into pots and the pots were left to stand at room temperature.

After 24 hours, the test insects were introduced into the treated soil, and after a further 2 to 7 days the degree of effectiveness of the active compound was determined in % by counting the dead and the live test insects. The degree of effectiveness was 100% if all the test insects had been killed and 0% if just as many test insects were still alive as in the case of the untreated control.

(4) In tests with *Phorbia antiqua* maggots in the soil, for example, the compounds (3) and (11) gave a degree of destruction of 100% in an experiment using a concentration of 1.5 ppm.

(5) In tests with *Tenebrio molitor* larvae in the soil, for example, the compounds (2), (7) and (10) showed a degree of destruction of 100% in an experiment using a concentration of 20 ppm.

EXAMPLES 6 AND 7

Critical concentration test/root-systemic action
(6) Test insect: *Phaedon cochleariae* larvae
(7) Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l), being decisive. The treated soil was filled into pots and these were planted with cabbage (Brassica oleracea). The active compound could in this way be taken up from the soil by the roots of the plants and be transported into the leaves.

To demonstrate the root-systemic effect, exclusively the leaves were infested with the abovementioned test animals after 7 days. After a further 2 days, the evaluation was made by counting or estimating the dead insects. The root-systemic action of the active compound was deduced from the mortality figures. It was 100% if all the test insects had been killed and 0% if just as many test insects were still alive as in the case of the untreated control.

(6) In the test with *Phaedon cochleariae* larvae, for example, the compounds (2), (3), (5) and (6) gave a degree of destruction of 100% in an experiment using a concentration of 10 ppm.

(7) In tests with *Myzus persicae*, for example, the compound (3) gave a degree of destruction of 100% in an experiment using a concentration of 10 ppm.

It will be appreciated that the instant specification and examples are set forth by way of illustration and not limitation, and that various modifications and changes may be made without departing from the spirit and scope of the present invention.

We claim:

1. An N-phosphonylcarbonyl-N-methylcarbamic acid ester of the formula $$\begin{array}{c} R^1-O \quad O \quad O \quad CH_3 \quad O \\ \diagdown \parallel \quad \parallel \quad | \quad \parallel \\ P-C-N-\!-\!-C-O-R^3 \\ \diagup \\ R^2-O \end{array}$$

in which
R¹ and R² can be identical or different and each represents straight-chain or branched alkyl with 1–8 C atoms, alkenyl with 3–6 C atoms or alkynyl with 3–6 C atoms, it being possible for $R^1$ and $R^2$ optionally to be substituted by 1–3 halogen atoms, and $R^3$ represents alkyl with 1–4 C atoms, phenyl, naphthyl, benzodioxolanyl dihydrobenzofuranyl or indanyl, it being possible for any of these radicals to carry one or more substituents selected from alkyl, alkenyl, alkynyl, alkoxy, alkenoxy, alkynoxy, alkylmercapto, alkenylmercapto, alkynylmercapto and dialkylamino with in each case up to 4 C atoms, and trihalogenomethyl, halogen, nitro, cyano, cycloalkyl, formamidino, dioxanyl and dioxolanyl, or $R^3$ represents the radical of the formula

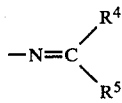

in which $R^4$ and $R^5$ can be identical or different and each represents alkyl, alkoxy or alkylthio, with in each case 1 to 4 carbon atoms, cyano, alkoxycarbonyl or alkylthioalkyl with 2 to 4 carbon atoms, dialkylcarbamoyl or dialkoxyphosphonyl, with 1 to 4 carbon atoms per alkyl group, or triazolyl, or $R^4$ and $R^5$, together with the C atom to which they are bonded, form a dithiolane, dithiane, oxythiolane or oxathiane ring which is optionally substituted by methyl or phenyl.

2. An N-phosphonylcarbonyl-N-methylcarbamic acid ester according to claim 1, in which $R^1$ and $R^2$ represent methyl, ethyl, 2-chloroethyl, octyl, allyl or propargyl and $R^3$ represents methyl, or represents phenyl which optionally carries one or more substituents selected from alkyl with 1 to 3 C atoms, alkoxy with 1 to 3 C atoms, methylthio, dioxolanyl and methyl-substituted dioxolanyl, or represents benzodioxolanyl or dihydrobenzofuranyl, it being possible for either of these radicals optionally to be substituted by methyl, or $R^3$ represents naphthyl or the imino radical of the formula

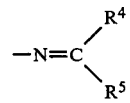

wherein $R^4$ and $R^5$ represent alkyl with 1 to 4 C atoms, alkylthioalkyl with 2 to 4 carbon atoms, methylthio, cyano, dimethylaminocarbonyl or ethoxycarbonyl, or $R^4$ and $R^5$, together with the C atoms to which they are bonded, form a dithiolane ring.

3. An N-phosphonylcarbonyl-N-methylcarbamic acid ester according to claim 1, wherein such ester is 2,3-dihydro-2,2-dimethyl-7-benzofuranyl N-dimethoxyphosphonylcarbonyl-N-methyl-carbamate of the formula

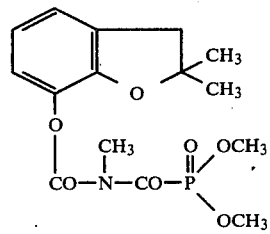

4. An N-phosphonylcarbonyl-N-methylcarbamic acid ester according to claim 1, wherein such ester is 2,3-dihydro-2,2-dimethyl-7-benzofuranyl N-diethoxyphosphonylcarbonyl-N-methyl-carbamate of the formula

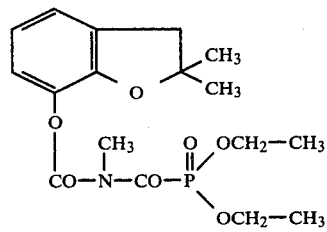

5. An N-phosphonylcarbonyl-N-methylcarbamic acid ester according to claim 1, wherein such ester is 2,3-dihydro-2,2-dimethyl-7-benzofuranyl N-di-($\beta$-chloroethoxy)-phosphonylcarbonyl-N-methyl-carbamate of the formula

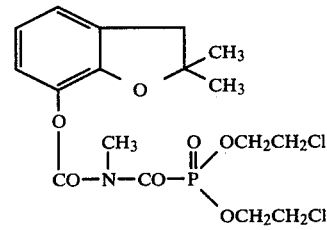

6. An N-phosphonylcarbonyl-N-methylcarbamic acid ester according to claim 1, wherein such ester is O-(N-dimethoxyphosphonylcarbonyl-N-methyl-carbamyl)-hydroxamo-thioacetic acid S-methyl ester of the formula

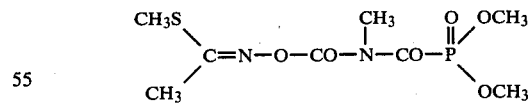

7. An N-phosphonylcarbonyl-N-methylcarbamic acid ester according to claim 1, wherein such ester is (-(N-dimethoxyphosphonylcarbonyl-N-methyl-carbamyl)-hydroxamo-($\alpha$-trimethyl-$\alpha'$-methylthio)-acetone of the formula

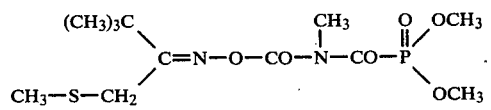

8. An arthropodicidal composition comprising an arthropodicidally effective amount of an ester according to claim 1 in admixture with a diluent.

9. A method of combating, anthropods comprising applying to the arthropods, or to a habitat thereof, an arthropodically effective amount of an ester according to claim 1.

10. The method according to claim 9, wherein the ester is:

2,3-dihydro-2,2-dimethyl-7-benzofuranyl N-dimethoxy-phosphonylcarbonyl-N-methyl-carbamate, 2,3-dihydro-2,2-dimethyl-7-benzofuranyl N-diethoxyphosphonylcarbonyl-N-methyl-carbamate, 2,3-dihydro-2,2-dimethyl-7-benzofuranyl N-di-(chloroethoxy)-phosphonylcarbonyl-N-methyl-carbamate, O-(N-dimethoxyphosphonylcarbonyl-N-methyl-carbamyl)-hydroxamo-thioacetic acid S-methyl ester or O-(N-dimethoxyphosphonylcarbonyl-N-methyl-carbamyl)-hydroxamo-($\alpha$-trimethyl-$\alpha'$-methylthio)-acetone.

* * * * *